(12) United States Patent
Chintalapoodi

(10) Patent No.: US 10,126,892 B2
(45) Date of Patent: Nov. 13, 2018

(54) MOISTURE MANAGEMENT

(71) Applicant: Synaptics Incorporated, San Jose, CA (US)

(72) Inventor: Prakriti Chintalapoodi, Sunnyvale, CA (US)

(73) Assignee: Synaptics Incorporated, San Jose, CA (US)

( * ) Notice: Subject to any disclaimer, the term of this patent is extended or adjusted under 35 U.S.C. 154(b) by 100 days.

(21) Appl. No.: 15/087,653

(22) Filed: Mar. 31, 2016

(65) Prior Publication Data

US 2017/0269729 A1    Sep. 21, 2017

Related U.S. Application Data

(60) Provisional application No. 62/309,194, filed on Mar. 16, 2016.

(51) Int. Cl.
*G06F 3/044* (2006.01)
*G06F 3/041* (2006.01)
*G01N 27/22* (2006.01)

(52) U.S. Cl.
CPC ........... *G06F 3/044* (2013.01); *G01N 27/223* (2013.01); *G06F 3/0416* (2013.01)

(58) Field of Classification Search
CPC ........ G06F 3/044; G06F 3/0416; G06F 3/041; G01N 27/223; G01R 27/2605; G01D 5/24
See application file for complete search history.

(56) References Cited

U.S. PATENT DOCUMENTS

| | | | |
|---|---|---|---|
| 5,861,583 A | 1/1999 | Schediwy et al. | |
| 7,583,092 B2 | 9/2009 | Reynolds et al. | |
| 8,462,135 B1 | 6/2013 | Xiao et al. | |
| 8,482,536 B1 | 7/2013 | Young | |
| 8,487,907 B2 | 7/2013 | Huang et al. | |
| 8,519,975 B2 | 8/2013 | Huang et al. | |
| 8,525,801 B2 | 9/2013 | Huang et al. | |
| 8,564,553 B2 | 10/2013 | Yeh et al. | |
| 8,592,698 B2 | 11/2013 | Hung et al. | |
| 8,605,056 B2 | 12/2013 | Mai et al. | |
| 8,896,328 B2 | 11/2014 | Reynolds et al. | |
| 9,141,208 B2 * | 9/2015 | Park | G06F 3/0488 |
| 9,310,934 B2 * | 4/2016 | Ng | G06F 3/0418 |
| 9,880,655 B2 * | 1/2018 | O'Connor | G06F 3/0416 |
| 2009/0009195 A1 | 1/2009 | Seguine | |
| 2009/0315841 A1 | 12/2009 | Cheng et al. | |
| 2010/0188364 A1 | 7/2010 | Lin et al. | |
| 2011/0007021 A1 | 1/2011 | Bernstein et al. | |
| 2011/0025629 A1 | 2/2011 | Grivna et al. | |
| 2011/0050632 A1 | 3/2011 | Lin et al. | |
| 2011/0050633 A1 | 3/2011 | Lin et al. | |
| 2011/0050634 A1 | 3/2011 | Lin et al. | |

(Continued)

*Primary Examiner* — Jennifer Mehmood
*Assistant Examiner* — Sardis F Azongha
(74) *Attorney, Agent, or Firm* — Ferguson Braswell Fraser Kubasta PC

(57) ABSTRACT

A method for moisture detection includes obtaining absolute capacitive sensor data, and processing circuitry, determining a contiguous region in a capacitive image generated based on the absolute capacitive sensor data, determining a concavity parameter of the contiguous region, and detecting a presence of moisture based at least in part on the concavity parameter. The method further includes operating based on a presence of moisture.

20 Claims, 8 Drawing Sheets

(56) References Cited

U.S. PATENT DOCUMENTS

| | | |
|---|---|---|
| 2012/0044199 A1 | 2/2012 | Karpin et al. |
| 2012/0050180 A1 | 3/2012 | King et al. |
| 2012/0050214 A1 | 3/2012 | Kremin et al. |
| 2012/0306806 A1 | 12/2012 | Yang et al. |
| 2013/0027346 A1 | 1/2013 | Yarosh et al. |
| 2013/0154996 A1 | 6/2013 | Trend et al. |
| 2013/0162583 A1 | 6/2013 | Simmons et al. |
| 2013/0176280 A1 | 7/2013 | Wu et al. |
| 2013/0181916 A1 | 7/2013 | Huang et al. |
| 2013/0215047 A1 | 8/2013 | Wu et al. |
| 2013/0215053 A1 | 8/2013 | Lin et al. |
| 2013/0222047 A1 | 8/2013 | Huang et al. |
| 2013/0241870 A1 | 9/2013 | Lin et al. |
| 2013/0249852 A1 | 9/2013 | Lin et al. |
| 2013/0257767 A1 | 10/2013 | Wu et al. |
| 2013/0257797 A1 | 10/2013 | Wu et al. |
| 2013/0299330 A1 | 11/2013 | Tao et al. |
| 2013/0307811 A1 | 11/2013 | Hanssen et al. |
| 2013/0307812 A1 | 11/2013 | Hanssen et al. |
| 2013/0307813 A1 | 11/2013 | Hanssen et al. |
| 2015/0116253 A1 | 4/2015 | Schwartz |
| 2015/0162932 A1 * | 6/2015 | Page ................ G01R 27/2605 324/658 |
| 2015/0261377 A1 | 9/2015 | Reynolds et al. |
| 2015/0346859 A1 | 12/2015 | Shen |
| 2015/0378496 A1 | 12/2015 | Vandermeijden et al. |

* cited by examiner

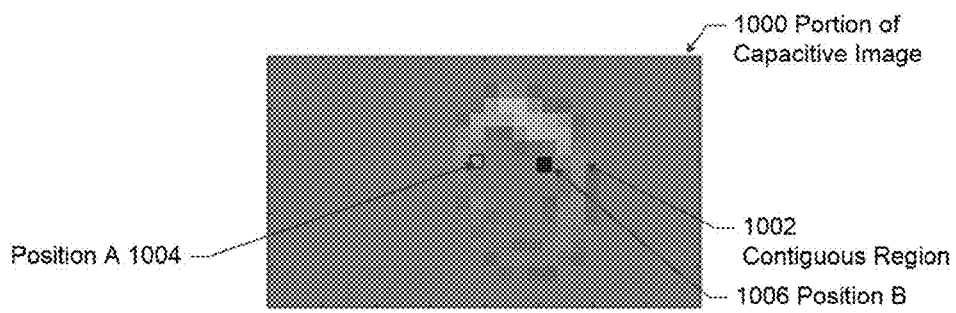
*FIG. 10.1*
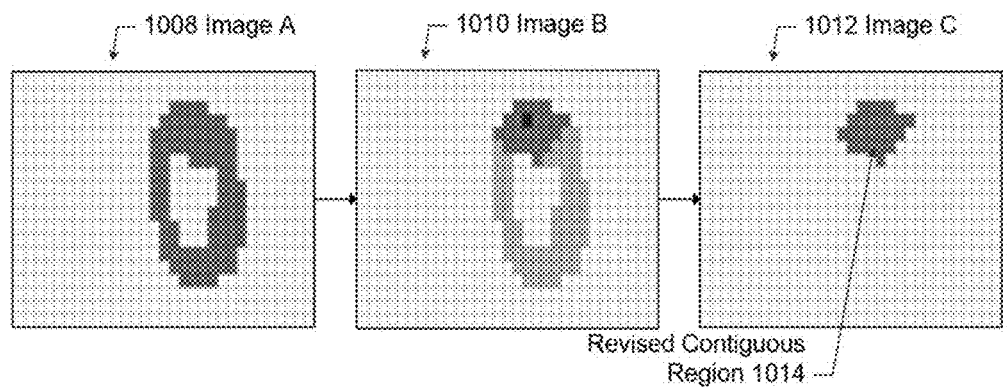
*FIG. 10.2*
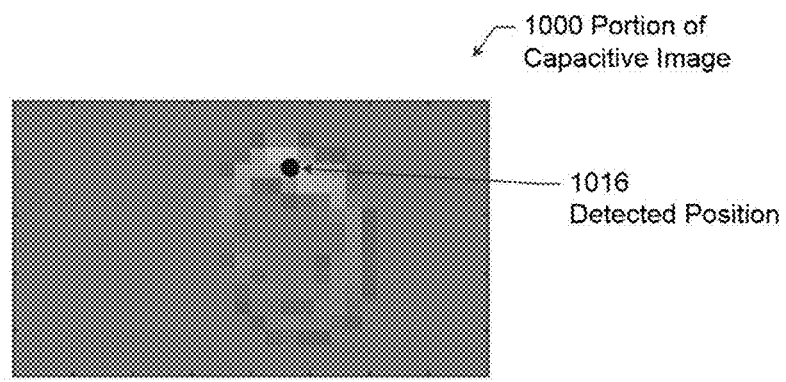
*FIG. 10.3*

MOISTURE MANAGEMENT

CROSS REFERENCE TO RELATED APPLICATIONS

This application claims priority under 35 U.S.C. § 119(e) to U.S. Provisional Patent Application Ser. No. 62/309,194, filed on Mar. 16, 2016 and entitled, "MOISTURE MANAGEMENT", which is incorporated herein by reference in its entirety.

FIELD

This invention generally relates to electronic devices.

BACKGROUND

Input devices, including proximity sensor devices (also commonly called touchpads or touch sensor devices), are widely used in a variety of electronic systems. A proximity sensor device typically includes a sensing region, often demarked by a surface, in which the proximity sensor device determines the presence, location and/or motion of one or more input objects. Proximity sensor devices may be used to provide interfaces for the electronic system. For example, proximity sensor devices are often used as input devices for larger computing systems (such as opaque touchpads integrated in, or peripheral to, notebook or desktop computers). Proximity sensor devices are also often used in smaller computing systems (such as touch screens integrated in cellular phones).

SUMMARY

In general, in one aspect, one or more embodiments relate to a processing system for moisture detection. The processing system includes sensor circuitry for obtaining absolute capacitive sensor data, and processing circuitry. The processing circuitry is configured to determine a contiguous region in a capacitive image generated based on the absolute capacitive sensor data, determine a concavity parameter of the contiguous region, and detect a presence of moisture based at least in part on the concavity parameter. The processing circuitry is further configured to operate based on a presence of moisture.

In general, in one aspect, one or more embodiments relate to a method for moisture detection. The method includes obtaining absolute capacitive sensor data, and processing circuitry, determining a contiguous region in a capacitive image generated based on the absolute capacitive sensor data, determining a concavity parameter of the contiguous region, and detecting a presence of moisture based at least in part on the concavity parameter. The method further includes operating based on a presence of moisture.

In general, in one aspect, one or more embodiments relate to a processing system for moisture detection. The processing system includes sensor circuitry for obtaining absolute capacitive sensor data, and processing circuitry. The processing circuitry is configured to determine a contiguous region in a capacitive image generated based on the absolute capacitive sensor data, determine a concavity parameter of the contiguous region, and detect a presence of moisture based at least in part on the concavity parameter. The processing circuitry is further configured to operate based on a presence of moisture.

Other aspects of the invention will be apparent from the following description and the appended claims.

BRIEF DESCRIPTION OF DRAWINGS

The preferred exemplary embodiment of the present invention will hereinafter be described in conjunction with the appended drawings, where like designations denote like elements, and:

FIGS. 8, 9, 10.1, 10.2, and 10.3 are examples in accordance with one or more embodiments of the invention.

DETAILED DESCRIPTION

The following detailed description is merely exemplary in nature, and is not intended to limit the invention or the application and uses of the invention. Furthermore, there is no intention to be bound by any expressed or implied theory presented in the preceding technical field, background, brief summary or the following detailed description.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Various embodiments of the present invention provide input devices and methods that facilitate improved usability. In particular, one or more embodiments are directed to moisture management. Moisture is the presence of a substance in liquid form (i.e., liquid substance) on the surface sensing region that may affect a capacitive image at least when an input object is presence. Moisture may be in the form of one or more droplets and/or puddles of virtually any size on the surface sensing region. For example, moisture may be a fine mist on the surface sensing region. Moisture management may include moisture detection and operating according to whether moisture is presence. Moisture detection involves determining a presence of moisture based on indicators in a capacitive image.

Figure 1:
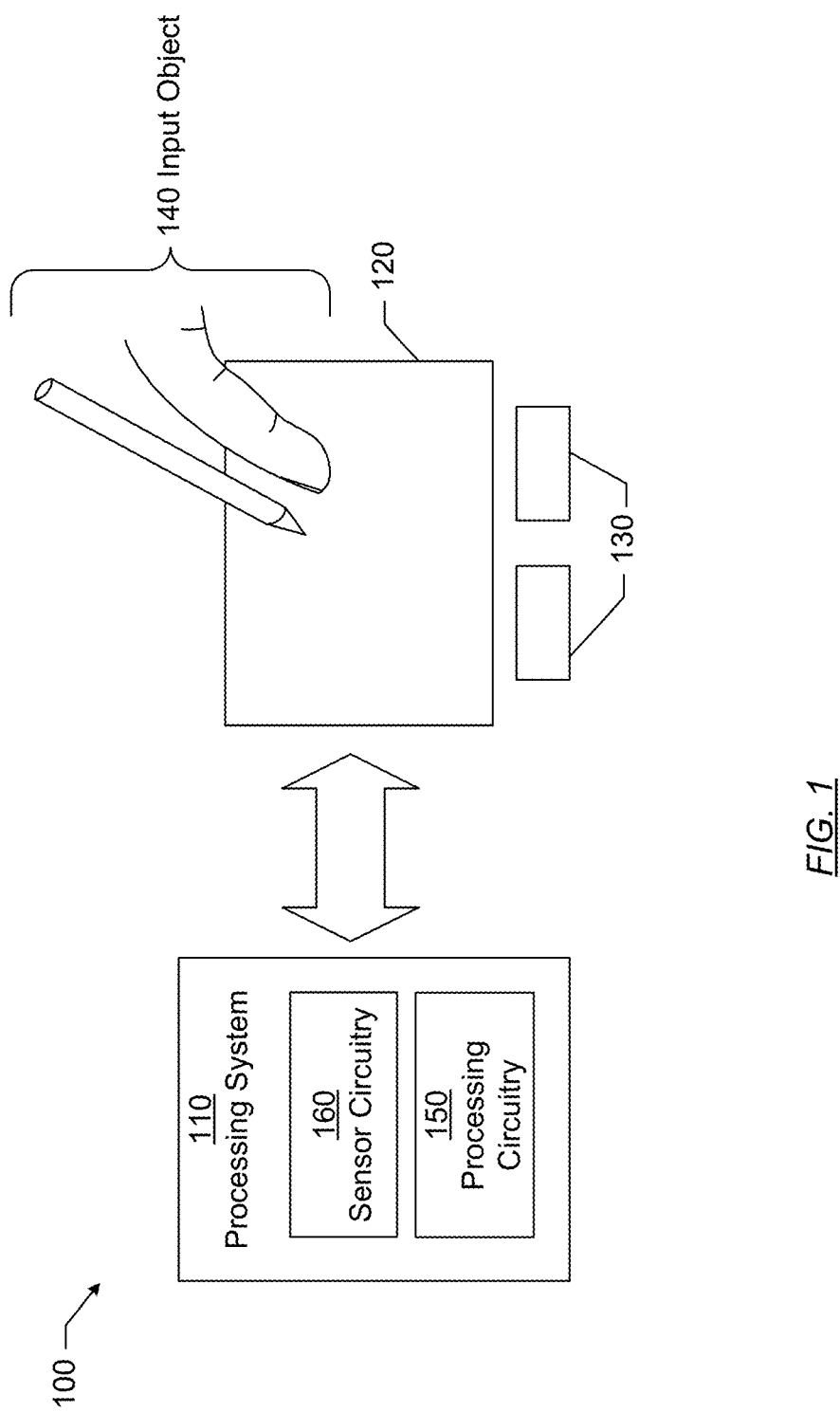
FIG. 1 is a block diagram of an example system that includes an input device in accordance with an embodiment of the invention.

Turning now to the figures, FIG. 1 is a block diagram of an exemplary input device (100), in accordance with embodiments of the invention. The input device (100) may be configured to provide input to an electronic system (not shown). As used in this document, the term "electronic system" (or "electronic device") broadly refers to any system capable of electronically processing information. Some non-limiting examples of electronic systems include personal computers of all sizes and shapes, such as desktop computers, laptop computers, netbook computers, tablets, web browsers, e-book readers, and personal digital assistants (PDAs). Additional example electronic systems include composite input devices, such as physical keyboards that include input device (100) and separate joysticks or key switches. Further example electronic systems include peripherals, such as data input devices (including remote controls and mice), and data output devices (including display screens and printers). Other examples include remote terminals, kiosks, and video game machines (e.g., video game consoles, portable gaming devices, and the like). Other examples include communication devices (including cellular phones, such as smart phones), and media devices (including recorders, editors, and players such as televisions, set-top boxes, music players, digital photo frames, and digital cameras). Additionally, the electronic system could be a host or a slave to the input device.

The input device (100) may be implemented as a physical part of the electronic system, or may be physically separate from the electronic system. Further, portions of the input device (100) may be part of the electronic system. For example, all or part of the processing system may be implemented in the device driver of the electronic system. As appropriate, the input device (100) may communicate with parts of the electronic system using any one or more of the following: buses, networks, and other wired or wireless interconnections. Examples include I2C, SPI, PS/2, Universal Serial Bus (USB), Bluetooth, RF, and IRDA.

In FIG. 1, the input device (100) is shown as a proximity sensor device (also often referred to as a "touchpad" or a "touch sensor device") configured to sense input provided by one or more input objects (140) in a sensing region (120). Example input objects include fingers and styli, as shown in FIG. 1. Throughout the specification, the singular form of input object is used. Although the singular form is used, multiple input objects may exist in the sensing region (120). Further, which particular input objects are in the sensing region may change over the course of one or more gestures. To avoid unnecessarily complicating the description, the singular form of input object is used and refers to all of the above variations.

The sensing region (120) encompasses any space above, around, in and/or near the input device (100) in which the input device (100) is able to detect user input (e.g., user input provided by one or more input objects (140)). The sizes, shapes, and locations of particular sensing regions may vary widely from embodiment to embodiment.

In some embodiments, the sensing region (120) extends from a surface of the input device (100) in one or more directions into space until signal-to-noise ratios prevent sufficiently accurate object detection. The extension above the surface of the input device may be referred to as the above surface sensing region. The distance to which this sensing region (120) extends in a particular direction, in various embodiments, may be on the order of less than a millimeter, millimeters, centimeters, or more, and may vary significantly with the type of sensing technology used and the accuracy desired. Thus, some embodiments sense input that comprises no contact with any surfaces of the input device (100), contact with an input surface (e.g. a touch surface) of the input device (100), contact with an input surface of the input device (100) coupled with some amount of applied force or pressure, and/or a combination thereof. In various embodiments, input surfaces may be provided by surfaces of casings within which the sensor electrodes reside, by face sheets applied over the sensor electrodes or any casings, etc. In some embodiments, the sensing region (120) has a rectangular shape when projected onto an input surface of the input device (100).

The input device (100) may utilize any combination of sensor components and sensing technologies to detect user input in the sensing region (120). The input device (100) includes one or more sensing elements for detecting user input. As several non-limiting examples, the input device (100) may use capacitive, elastive, resistive, inductive, magnetic, acoustic, ultrasonic, and/or optical techniques.

Some implementations are configured to provide images that span one, two, three, or higher-dimensional spaces. Some implementations are configured to provide projections of input along particular axes or planes. Further, some implementations may be configured to provide a combination of one or more images and one or more projections.

In some resistive implementations of the input device (100), a flexible and conductive first layer is separated by one or more spacer elements from a conductive second layer. During operation, one or more voltage gradients are created across the layers. Pressing the flexible first layer may deflect it sufficiently to create electrical contact between the layers, resulting in voltage outputs reflective of the point(s) of contact between the layers. These voltage outputs may be used to determine positional information.

In some inductive implementations of the input device (100), one or more sensing elements pick up loop currents induced by a resonating coil or pair of coils. Some combination of the magnitude, phase, and frequency of the currents may then be used to determine positional information.

In some capacitive implementations of the input device (100), voltage or current is applied to create an electric field. Nearby input objects cause changes in the electric field, and produce detectable changes in capacitive coupling that may be detected as changes in voltage, current, or the like.

Some capacitive implementations utilize arrays or other regular or irregular patterns of capacitive sensing elements to create electric fields. In some capacitive implementations, separate sensing elements may be ohmically shorted together to form larger sensor electrodes. Some capacitive implementations utilize resistive sheets, which may be uniformly resistive.

Some capacitive implementations utilize "self capacitance" (or "absolute capacitance") sensing methods based on changes in the capacitive coupling between sensor electrodes and an input object. In various embodiments, an input object near the sensor electrodes alters the electric field near the sensor electrodes, thus changing the measured capacitive coupling. In one implementation, an absolute capacitance sensing method operates by modulating sensor electrodes with respect to a reference voltage (e.g., system ground), and by detecting the capacitive coupling between the sensor electrodes and input objects. The reference voltage may be a substantially constant voltage or a varying voltage and in various embodiments; the reference voltage may be system ground. Measurements acquired using absolute capacitance sensing methods may be referred to as absolute capacitive measurements.

Some capacitive implementations utilize "mutual capacitance" (or "trans capacitance") sensing methods based on changes in the capacitive coupling between sensor electrodes. In various embodiments, an input object near the sensor electrodes alters the electric field between the sensor electrodes, thus changing the measured capacitive coupling. In one implementation, a mutual capacitance sensing method operates by detecting the capacitive coupling between one or more transmitter sensor electrodes (also "transmitter electrodes" or "transmitter") and one or more receiver sensor electrodes (also "receiver electrodes" or "receiver"). Transmitter sensor electrodes may be modulated relative to a reference voltage (e.g., system ground) to transmit transmitter signals. Receiver sensor electrodes may be held substantially constant relative to the reference voltage to facilitate receipt of resulting signals. The reference voltage may be a substantially constant voltage and in various embodiments; the reference voltage may be system ground. In some embodiments, transmitter sensor electrodes may both be modulated. The transmitter electrodes are modulated relative to the receiver electrodes to transmit transmitter signals and to facilitate receipt of resulting signals. A resulting signal may include effect(s) corresponding to one or more transmitter signals, and/or to one or more sources of environmental interference (e.g., other electromagnetic signals). The effect(s) may be the transmitter signal, a change in the transmitter signal caused by one or more input objects and/or environmental interference, or other such effects. Sensor electrodes may be dedicated transmitters or receivers, or may be configured to both transmit and receive. Measurements acquired using mutual capacitance sensing methods may be referred to as mutual capacitance measurements.

Further, the sensor electrodes may be of varying shapes and/or sizes. The same shapes and/or sizes of sensor electrodes may or may not be in the same groups. For example, in some embodiments, receiver electrodes may be of the same shapes and/or sizes while, in other embodiments, receiver electrodes may be varying shapes and/or sizes.

In other embodiments, one or more of sensor electrodes are disposed on the same side or surface of the common substrate and are isolated from each other in the sensing region. The sensor electrodes may be disposed in a matrix array where each sensor electrode may be referred to as a matrix sensor electrode. The matrix array may correspond to a grid pattern. Each sensor electrode of sensor electrodes may be substantially similar in size and/or shape. In one embodiment, one or more of the sensor electrodes of the matrix array of sensor electrodes may vary in at least one of the size and shape. Each sensor electrode of the matrix array may correspond to a pixel of a capacitive image (i.e., capacitive pixel). Further, two or more sensor electrodes of the matrix array may correspond to a pixel of a capacitive image (i.e., capacitive pixel). In other words, a capacitive pixel is a location at which a measurement is acquired. In various embodiments, each sensor electrode of the matrix array may be coupled to a separate capacitive routing trace of a plurality of capacitive routing traces. In various embodiments, the sensor electrodes include one or more gird electrodes disposed between at least two sensor electrodes of the sensor electrodes. The grid electrode and at least one sensor electrode may be disposed on a common side of a substrate, different sides of a common substrate and/or on different substrates. In one or more embodiments, the sensor electrodes and the grid electrode(s) may encompass an entire voltage electrode of a display device. Although the sensor electrodes may be electrically isolated on the substrate, the electrodes may be coupled together outside of the sensing region (e.g., in a connection region). In one or more embodiments, a floating electrode may be disposed between the grid electrode and the sensor electrodes. In one particular embodiment, the floating electrode, the grid electrode and the sensor electrode include the entirety of a common electrode of a display device.

In any sensor electrode arrangement (e.g., the matrix array described above), the sensor electrodes may be operated by the input device for mutual capacitive sensing by dividing the sensor electrodes into transmitter and receiver electrodes. As another example, in any sensor electrode arrangement (e.g., the matrix array described above), the sensor electrodes may be operated by the input device for absolute capacitive sensing. As another example, in any sensor electrode arrangement, a mixture of absolute and mutual capacitance sensing may be used. Further, one or more of the sensor electrodes or the display electrodes (e.g., source, gate, or reference (Vcom) electrodes) may be used to perform shielding.

A set of measurements from the capacitive pixels form a capacitive frame. In other words, the capacitive frame represents the set of measurements acquired for a moment in time. The measurements include effects of the capacitance, an input object in the sensing region, and any background capacitance. The capacitive frame may include a capacitive image that is representative of the capacitive couplings at the pixels and/or include a capacitive profile that is representative of the capacitive couplings or along each sensor electrode. Multiple capacitive frames may be acquired over multiple time periods, and differences between them may be used to derive information about input in the sensing region. For example, successive capacitive frames acquired over successive periods of time can be used to track the motion(s) of one or more input objects entering, exiting, and within the sensing region.

The background capacitance of a sensor device is the capacitive frame associated with no input object in the sensing region. The background capacitance changes with the environment and operating conditions, and may be estimated in various ways. For example, some embodiments take "baseline frames" when no input object is determined to be in the sensing region, and use those baseline frames as estimates of their background capacitances.

Capacitive frames can be adjusted for the background capacitance of the sensor device for more efficient processing. Some embodiments accomplish this by "baselining" measurements of the capacitive couplings at the capacitive pixels to produce "baselined capacitive frames." That is, some embodiments compare the measurements forming capacitance frames with appropriate "baseline values" of "baseline frames", and determine changes from that baseline image.

In FIG. 1, a processing system (110) is shown as part of the input device (100). The processing system (110) is configured to operate the hardware of the input device (100) to detect input in the sensing region (120). The processing system (110) includes parts of, or all of, one or more integrated circuits (ICs) and/or other circuitry components. For example, a processing system for a mutual capacitance sensor device may include transmitter circuitry configured to transmit signals with transmitter sensor electrodes, and/or receiver circuitry configured to receive signals with receiver sensor electrodes. Further, a processing system for an absolute capacitance sensor device may include driver circuitry configured to drive absolute capacitance signals onto sensor electrodes, and/or receiver circuitry configured to receive signals with those sensor electrodes. In one or more embodiments, a processing system for a combined mutual and absolute capacitance sensor device may include any combination of the above described mutual and absolute capacitance circuitry. In some embodiments, the processing system (110) also includes electronically-readable instructions, such as firmware code, software code, and/or the like. In some embodiments, components composing the processing system (110) are located together, such as near sensing element(s) of the input device (100). In other embodiments, components of processing system (110) are physically separate with one or more components close to the sensing element(s) of the input device (100), and one or more components elsewhere. For example, the input device (100) may be a peripheral coupled to a computing device, and the processing system (110) may include software configured to run on a central processing unit of the computing device and one or more ICs (perhaps with associated firmware) separate from the central processing unit. As another example, the input device (100) may be physically integrated in a mobile device, and the processing system (110) may include circuits and firmware that are part of a main processor of the mobile device. In some embodiments, the processing system (110) is dedicated to implementing the input device (100). In other embodiments, the processing system (110) also performs other functions, such as operating display screens, driving haptic actuators, etc.

The processing system (110) may be implemented as a set of modules that handle different functions of the processing system (110). Each module may include circuitry that is a part of the processing system (110), firmware, software, or a combination thereof. In various embodiments, different combinations of modules may be used. For example, as shown in FIG. 1, the processing system (110) may include processing circuitry (150) and sensor circuitry (160). The processing circuitry (150) may correspond to hardware circuitry, such as a central processing unit, an application specific integrated circuit, or other hardware. The processing circuitry (150) may include functionality to detect a presence of moisture, operate based on the presence of moisture, determine when at least one input object is in a sensing region, determine signal to noise ratio, determine positional information of an input object, identify a gesture, determine an action to perform based on the gesture, a combination of gestures or other information, perform other operations, and/or perform any combination of operations.

The sensor circuitry (160) may correspond to hardware circuitry, such as a central processing unit, an application specific integrated circuit, or other hardware that includes functionality to drive the sensor electrodes. For example, the sensor module (160) may include sensory circuitry that is coupled to the sensing elements.

Although FIG. 1 shows the processing circuitry (150) and the sensor circuitry (160) as separate components, all or part of the processing circuitry (150) may be the same as the sensor circuitry (160). Further, although FIG. 1 shows only processing circuitry (150) and sensor circuitry (160), alternative or additional hardware circuitry may exist in accordance with one or more embodiments of the invention. Such alternative or additional circuitry may correspond to distinct circuitry or sub-circuitry than one or more of the circuitry discussed above. Example alternative or additional circuitry includes hardware operation circuitry for operating hardware such as sensor electrodes and display screens, data processing circuitry for processing data such as sensor signals and positional information, reporting circuitry for reporting information, and identification circuitry configured to identify gestures, such as mode changing gestures, and mode changing circuitry for changing operation modes. Further, the various circuitry may be combined in separate integrated circuits. For example, a first circuitry may be comprised at least partially within a first integrated circuit, and a separate circuitry may be comprised at least partially within a second integrated circuit. Further, portions of a single circuitry may span multiple integrated circuits. In some embodiments, the processing system as a whole may perform the operations of the various circuitry.

In some embodiments, the processing system (110) responds to user input (or lack of user input) in the sensing region (120) directly by causing one or more actions. Example actions include changing operation modes, as well as graphical user interface (GUI) actions such as cursor movement, selection, menu navigation, and other functions. In some embodiments, the processing system (110) provides information about the input (or lack of input) to some part of the electronic system (e.g. to a central processing system of the electronic system that is separate from the processing system (110), if such a separate central processing system exists). In some embodiments, some part of the electronic system processes information received from the processing system (110) to act on user input, such as to facilitate a full range of actions, including mode changing actions and GUI actions.

For example, in some embodiments, the processing system (110) operates the sensing element(s) of the input device (100) to produce electrical signals indicative of input (or lack of input) in the sensing region (120). The processing system (110) may perform any appropriate amount of processing on the electrical signals in producing the information provided to the electronic system. For example, the processing system (110) may digitize analog electrical signals obtained from the sensor electrodes. As another example, the processing system (110) may perform filtering or other signal conditioning. As yet another example, the processing system (110) may subtract or otherwise account for a baseline, such that the information reflects a difference between the electrical signals and the baseline. As yet further examples, the processing system (110) may determine positional information, recognize inputs as commands, recognize handwriting, and the like.

"Positional information" as used herein broadly encompasses absolute position, relative position, velocity, acceleration, and other types of spatial information. Exemplary "zero-dimensional" positional information includes near/far or contact/no contact information. Exemplary "one-dimensional" positional information includes positions along an axis. Exemplary "two-dimensional" positional information includes motions in a plane. Exemplary "three-dimensional" positional information includes instantaneous or average velocities in space. Further examples include other representations of spatial information. Historical data regarding one or more types of positional information may also be determined and/or stored, including, for example, historical data that tracks position, motion, or instantaneous velocity over time.

In some embodiments, the input device (100) is implemented with additional input components that are operated by the processing system (110) or by some other processing system. These additional input components may provide redundant functionality for input in the sensing region (120), or some other functionality. FIG. 1 shows buttons (130) near the sensing region (120) that may be used to facilitate selection of items using the input device (100). Other types of additional input components include sliders, balls, wheels, switches, and the like. Conversely, in some embodiments, the input device (100) may be implemented with no other input components.

In some embodiments, the input device (100) includes a touch screen interface, and the sensing region (120) overlaps at least part of an active area of a display screen. For example, the input device (100) may include substantially transparent sensor electrodes overlaying the display screen and provide a touch screen interface for the associated electronic system. The display screen may be any type of dynamic display capable of displaying a visual interface to a user, and may include any type of light emitting diode (LED), organic LED (OLED), cathode ray tube (CRT), liquid crystal display (LCD), plasma, electroluminescence (EL), or other display technology. The input device (100) and the display screen may share physical elements. For example, some embodiments may utilize some of the same electrical components for displaying and sensing. In various embodiments, one or more display electrodes of a display device may be configured for both display updating and input sensing. As another example, the display screen may be operated in part or in total by the processing system (110).

In various embodiments, the input device (100) may include one or more sensor electrodes configured for both display updating and input sensing. For example, at least one sensor electrode that is used for input sensing may comprise one or more display electrodes of the display device that are used in updating the display. Further, the display electrode may include one or more of segments of a Vcom electrode (common electrodes), source drive lines (electrodes), gate line (electrodes), an anode sub-pixel electrode or cathode pixel electrode, or any other display element. These display electrodes may be disposed on an appropriate display screen substrate. For example, the display electrodes may be disposed on a transparent substrate (a glass substrate, TFT glass, or any other transparent material) in some display screens (e.g., In Plane Switching (IPS), Fringe Field Switching (FFS) or Plane to Line Switching (PLS) Organic Light Emitting Diode (OLED)), on the bottom of the color filter glass of some display screens (e.g., Patterned Vertical Alignment (PVA) Multi-domain Vertical Alignment (MVA), IPS and FFS), over an cathode layer (OLED), etc. In such embodiments, the display electrode can also be referred to as a "combination electrode", since it performs multiple functions. In various embodiments, each of the sensor electrodes includes one or more display electrodes associated with a pixel or sub pixel. In other embodiments, at least two sensor electrodes may share at least one display electrode associated with a pixel or sub-pixel.

In various embodiments, a first sensor electrode includes one or more display electrodes configured for display updating and capacitive sensing and a second sensor electrode may be configured for capacitive sensing and not for display updating. The second sensor electrode may be disposed between substrates of the display device or external from the display device. In some embodiments, all of the sensor electrodes may include one or more display electrodes configured for display updating and capacitive sensing.

Processing system (110) may be configured to perform input sensing and display updating during at least partially overlapping periods. For example, a processing system (110) may simultaneously drive a first display electrode for both display updating and input sensing. In another example, processing system (110) may simultaneously drive a first display electrode for display updating and a second display electrode for input sensing. In some embodiments, processing system (110) is configured to perform input sensing and display updating during non-overlapping periods. The non-overlapping periods may be referred to as non-display update periods. The non-display update periods may occur between display line update periods of common display frame and be at least as long as a display line update period. Further, the non-display update periods may occur between display line update periods of a common display frame and be one of longer than or shorter than a display line update period. In some embodiments, the non-display update periods may occur at the beginning of a display frame and/or between display frames. Processing system (110) may be configured to drive one or more of the sensor electrodes and/or the display electrodes with a shield signal. The shield signal may comprise one of a constant voltage signal or a varying voltage signal (guard signal). Further, one or more of the sensor electrodes and/or display electrodes may be electrically floated.

It should be understood that while many embodiments of the invention are described in the context of a fully-functioning apparatus, the mechanisms of the present invention are capable of being distributed as a program product (e.g., software) in a variety of forms. For example, the mechanisms of the present invention may be implemented and distributed as a software program on information-bearing media that are readable by electronic processors (e.g., non-transitory computer-readable and/or recordable/writable information bearing media that is readable by the processing system (110)). Additionally, the embodiments of the present invention apply equally regardless of the particular type of medium used to carry out the distribution. For example, software instructions in the form of computer readable program code to perform embodiments of the invention may be stored, in whole or in part, temporarily or permanently, on a non-transitory computer-readable storage medium. Examples of non-transitory, electronically-readable media include various discs, physical memory, memory, memory sticks, memory cards, memory modules, and or any other computer readable storage medium. Electronically-readable media may be based on flash, optical, magnetic, holographic, or any other storage technology.

Although not shown in FIG. 1, the processing system, the input device, and/or the host system may include one or more computer processor(s), associated memory (e.g., random access memory (RAM), cache memory, flash memory, etc.), one or more storage device(s) (e.g., a hard disk, an optical drive such as a compact disk (CD) drive or digital versatile disk (DVD) drive, a flash memory stick, etc.), and numerous other elements and functionalities. The computer processor(s) may be an integrated circuit for processing instructions. For example, the computer processor(s) may be one or more cores or micro-cores of a processor. Further, one or more elements of one or more embodiments may be located at a remote location and connected to the other elements over a network. Further, embodiments of the invention may be implemented on a distributed system having several nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

While FIG. 1 shows a configuration of components, other configurations may be used without departing from the scope of the invention. For example, various components may be combined to create a single component. As another example, the functionality performed by a single component may be performed by two or more components.

Figure 2:
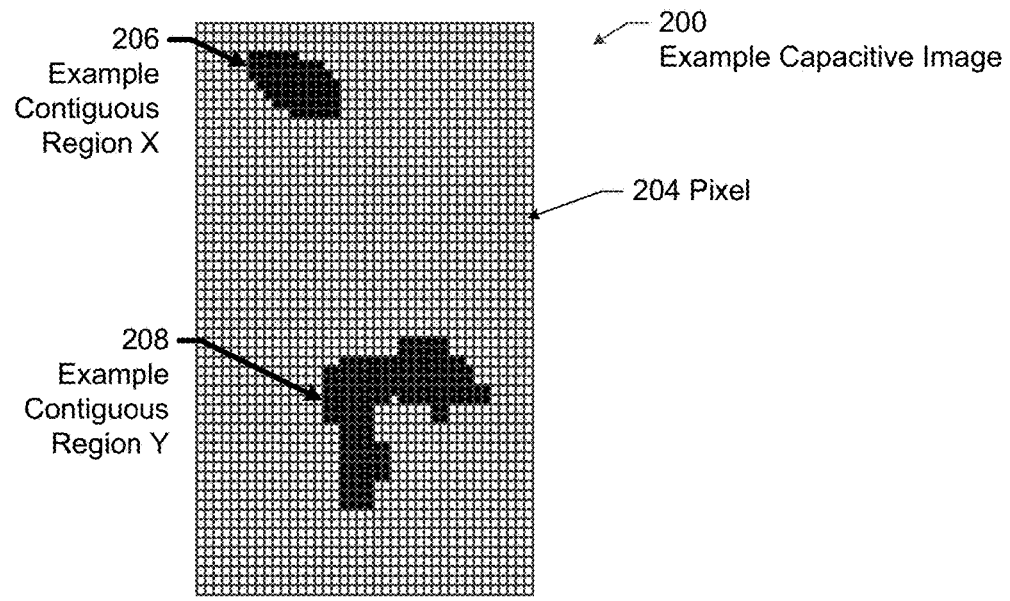
FIG. 2 is an example capacitive image in accordance with one or more embodiments of the invention.

FIG. 2 is an example capacitive image (200) with only contiguous regions shown in accordance with one or more embodiments of the invention. The example in FIG. 2 is for explanatory purposes only and not intended to limit the scope of the invention. For example, the dimensions of the capacitive image, number, size, shape, and other aspects of the contiguous regions, as well as any other aspects of FIG. 2 may change without departing from the scope of the invention.

Each box in FIG. 2 is a capacitive pixel (204) in the capacitive image (200) in which a measurement may be acquired. Pixels having measurements that do not satisfy a detection threshold are shown with white fill. The detection threshold is a threshold value or set of values by which an input object may be detected. The detection threshold may be a minimum, maximum or other value depending on the type of measurement values. Pixels having measurements that do not satisfy a detection threshold are shown with white fill. Pixels having measurements that do satisfy a detection threshold are shown with black fill.

As shown, the capacitive image (202) may include one or more contiguous regions (e.g., contiguous region X (206), contiguous region Y (208)). A contiguous region is a connected section of the sensing region in which each measurement in the connected section satisfies a threshold. In other words, the property of being contiguous refers to being adjoining or connected directly or indirectly by measurement values satisfying the same criteria (e.g., satisfying the detection threshold). The size, shape, and measurement values in the contiguous region may be affected by moisture as well as the shape, size, and positioning of input objects in the sensing region. One indicator of moisture is the concavity of the contiguous region. A concave shape is a shape in which a line segment connecting two points on the shape has at least one portion that is not on the shape. For example, while contiguous region X (206) is oval shaped and convex (i.e., not concave), contiguous region Y (208) is L-shaped and concave. The concavity of contiguous region Y (208) may be caused by an input object traversing and connecting droplets on the sensing region, by two input objects performing a pinching gesture, or by another cause. One or more embodiments analyze the contiguous regions and determine whether moisture is present.

Figure 3:
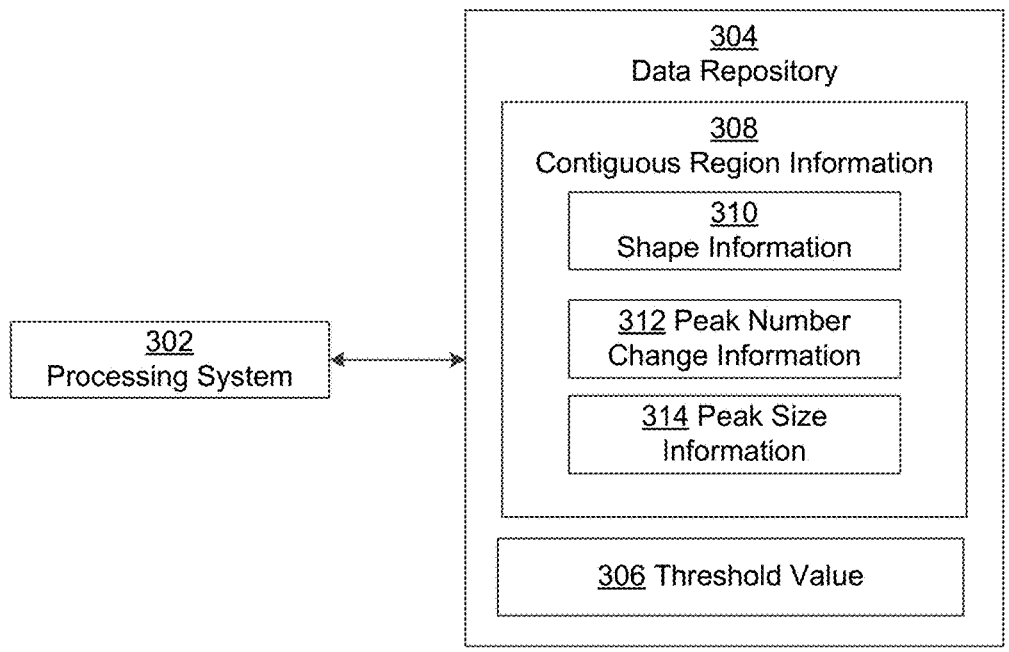
FIG. 3 is a block diagram of an example system in accordance with one or more embodiments of the invention.
Figure 4:
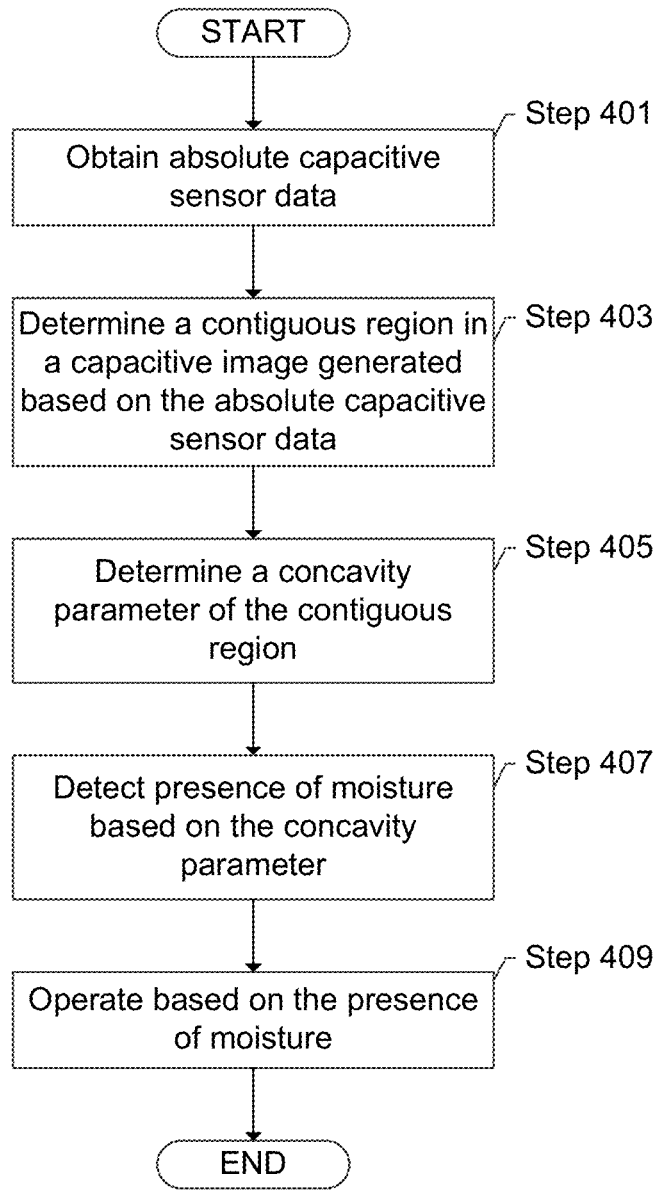
FIGS. 4, 5, 6, and 7 are example flowcharts in accordance with one or more embodiments of the invention.

FIG. 3 is a block diagram of an example system in accordance with one or more embodiments of the invention. As shown in FIG. 2, the system may include the processing system (302) operatively connected to a data repository (304). The processing system (302) may be the same or similar to the processing system (110) discussed above with reference to FIG. 1. The data repository (304) may be a part of the processing system (302) or a completely or partially distinct component from the processing system (302). The data repository (304) corresponds to any type of storage unit or device for storing data. For example, the data repository (304) may be cache memory, physical memory, flash memory, any other device, or any combination thereof.

In one or more embodiments of the invention, the data repository (304) includes a peak size threshold (306) and contiguous region information (308). The peak size threshold (306) is a threshold measurement value of a pixel by which the pixel is determined to be a part of a peak in the contiguous region. In one or more embodiments, a peak is a set of contiguous values around a peak value. For example, a peak value may be a local maximum measurement value. The peak is the contiguous section around the local maximum measurement value in the capacitive image. Although the description herein uses maximum, minimum or normalized values may be used. For example, in embodiments in which the greater negative value indicates the presence of an input object, a pixel may be determined to be part of the peak when the pixel is less than the peak size threshold. As shown, satisfying the threshold means being less than (or equal to) a minimum threshold, greater than (or equal to a maximum threshold), or being within normalized thresholds.

Contiguous region information (308) is information describing a contiguous region. Each contiguous region in a capacitive image may have individual contiguous region information. The same contiguous region in different capacitive images (e.g., from different sensing frames) may be consolidated into the same contiguous region information (308). The consolidation may be performed before, during, or after developing the contiguous region information. Further, the consolidation may be based on shape, size and positions of contiguous regions in successive capacitive images, whereby the successive capacitive images are generated in successive frames of sensing.

In one or more embodiments of the invention, the contiguous region information includes shape information (310), peak number change information (312), and peak size information (314). Shape information (310) defines the form of the contiguous region. For example, shape information may include the location within the capacitive image, perimeter, size of the contiguous region, circumference, other values describing the dimensions of the contiguous region, or any combination of values. Peak number change information (312) is information describing the change in the number of peaks for a particular contiguous region over successive frames. For example, peak number change information may include, for each frame, a number of peaks identifier identifying the number of peaks in the contiguous region in the frame. By way of another example, peak number change information may include, for each successive frame, a difference number of peaks identifier identifying the difference between the number of peaks in the contiguous region in the frame as compared to a previous frame. By way of another example, peak number change information may include, for each successive frame, a maximum difference number of peaks identifier identifying the maximum difference between the number of peaks in the contiguous region between consecutive frames. Other peak number change information may exist without departing from the scope of the invention.

Peak size information (314) identifies the size within the contiguous region that is part of a peak. Peak size information (314) may include the total peak size for all peaks in the contiguous region and/or an individual value for each peak. Further, peak size information may be a one dimensional size (e.g., maximum width of the peak) or a two dimensional size (e.g., area). Other peak size information may be used without departing from the scope of the invention.

FIGS. 4-7 are example flowcharts in accordance with one or more embodiments of the invention. While the various steps in these flowcharts are presented and described sequentially, one of ordinary skill will appreciate that some or all of the steps may be executed in different orders, may be combined or omitted, and some or all of the steps may be executed in parallel. Furthermore, the steps may be performed actively or passively. For example, some steps may be performed using polling or be interrupt driven in accordance with one or more embodiments of the invention. By way of an example, determination steps may not require a processor to process an instruction unless an interrupt is received to signify that condition exists in accordance with one or more embodiments of the invention. As another example, determination steps may be performed by performing a test, such as checking a data value to test whether the value is consistent with the tested condition in accordance with one or more embodiments of the invention.

In Step 401, absolute capacitive sensor data is obtained in accordance with one or more embodiments of the invention. In one or more embodiments of the invention, the absolute capacitive sensor data may be obtained from the data repository. In one or more embodiments, the absolute capacitive sensor data may be obtaining using the sensor circuitry and sensor electrodes. For example, the sensor circuitry may drive or modulate the sensor electrodes with respect to a reference voltage. Based on the modulating, the sensor circuitry may detect the absolute capacitance of the sensor electrodes, which may be affected by any input object, background capacitance, and/or moisture. In at least some embodiments, moisture is detectable in an absolute capacitive sensor data only when an input object is present. If moisture and an input object are present, the moisture may affect the measurement values in the absolute capacitive sensor data.

In Step 403, a contiguous region in the capacitive image, which is generated based on the absolute capacitive sensor data, is determined in accordance with one or more embodiments of the invention. By modulating each sensor electrode and obtaining measurements of the absolute capacitance, an absolute capacitive image may be generated. Preprocessing may be performed on the absolute capacitive image to remove background capacitance. For example, the preprocessing may include applying one or more temporal and spatial filters on the absolute capacitive image. The absolute capacitive image, during or after preprocessing, may be processed to determine contiguous regions in the capacitive image. For example, the processing may include identifying the pixels satisfying the detection threshold, and identifying contiguous regions of pixels that satisfy the detection threshold. In some embodiments, the contiguous regions may be processed to combine contiguous regions and/or remove invalid contiguous regions (e.g., regions that fail to satisfy a minimum size threshold). From the set of one or more contiguous regions in the capacitive image, a contiguous region is selected. Each contiguous region may be processed, such as until the presence of moisture is detected and/or until all contiguous regions are processed. Contiguous regions may be processed from largest to smallest in some embodiments of the invention.

In Step 405, a concavity parameter of the contiguous region is determined. Concavity may be determined by identifying internal angles of the contiguous region. If any internal angle is greater than 180 degrees, then the contiguous region is determined to be concave. Concavity may also be determined by determining whether any line segment exists that connects two points on the perimeter of the contiguous region and touches at least two additional points. Concavity may be determined based on the area and circumference of the contiguous region. In one or more embodiments of the invention, the concavity parameter is a Boolean value that specifies whether the contiguous region is concave or convex. In some embodiments, the concavity parameter is a scaled value that is based on the probability that the contiguous region is concave as compared to one or more erroneous measurements. For example, if the contiguous region includes only a small inward curvature, the concavity parameter may have a lower value than when the contiguous region has large inward curvature.

In Step 407, presence of moisture is detected based on the concavity parameter in accordance with one or more embodiments of the invention. In one or more embodiments of the invention, if the concavity parameter indicates a presence of moisture, then the moisture may be detected. In some embodiments, such as described in FIG. 5, additional indicators may also be used to detect the presence of moisture. The additional indicators may be primary or secondary to the concavity parameter.

In Step 409, based on the presence of moisture, the system operates in accordance with one or more embodiments of the invention. For example, the system may report the moisture to a host device. By way of another example, the system may mitigate the effects of the moisture in the capacitive image.

Figure 5:
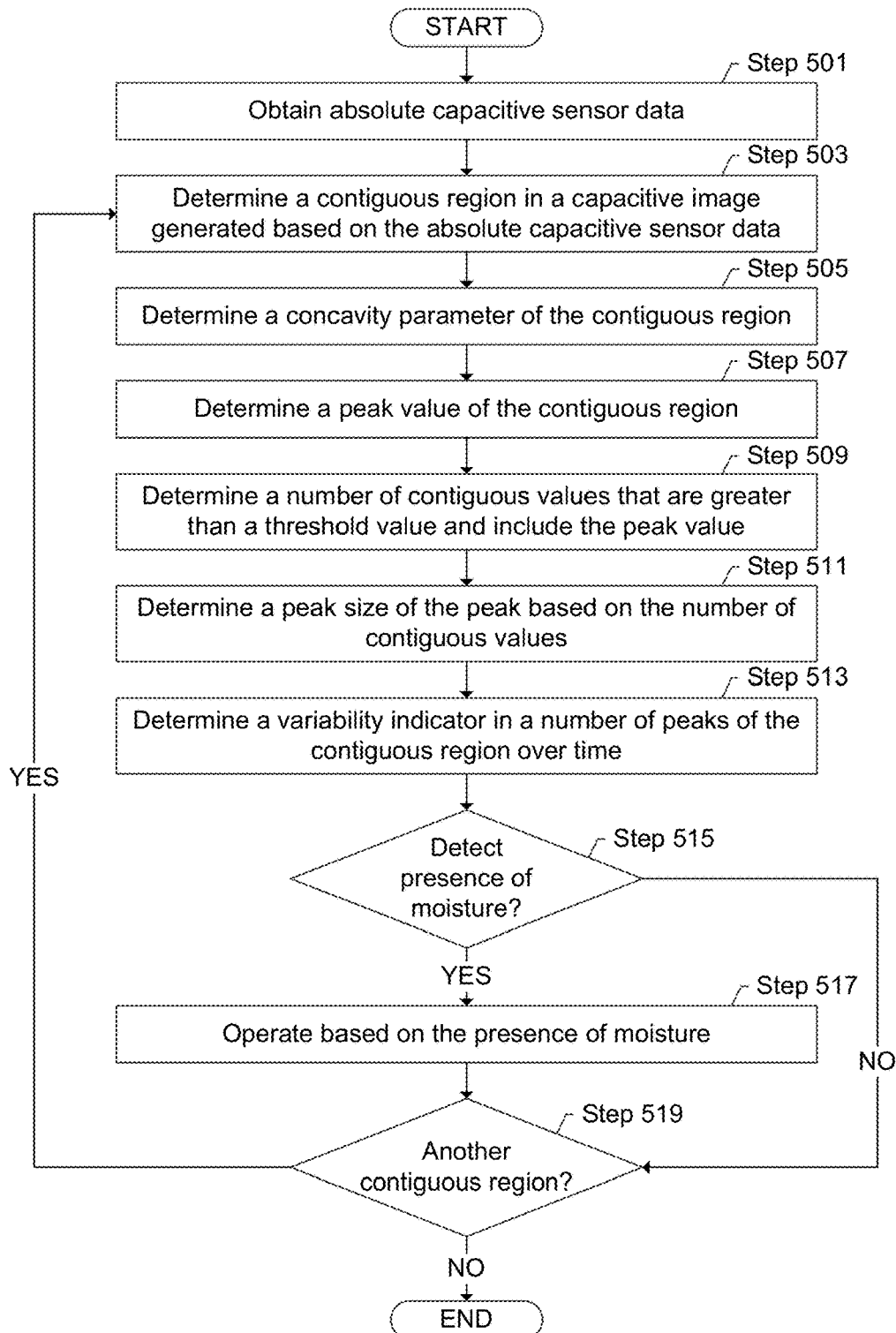

FIG. 5 shows a flowchart for moisture detection in accordance with one or more embodiments of the invention. In Step 501, absolute capacitive sensor data is obtained in accordance with one or more embodiments of the invention. In Step 503, a contiguous region in the capacitive image that is generated based on the absolute capacitive sensor data, is determined. The system may process two or more contiguous regions sequentially, in parallel, or in a combination of sequentially or in parallel. In Step 505, a concavity parameter of the contiguous region is determined. Steps 501, 503, and 505 may be performed in a same or similar manner discussed above with reference to Steps 401, 403, and 405 in FIG. 4.

In Step 507, a peak value of the contiguous region is determined in accordance with one or more embodiments of the invention. Determining a peak value may be performed by comparing each current measurement value with the neighbors of the measurement value. In the case of peak values being maximum, if the neighbor is greater than the current measurement value, then the neighbor is selected and the process may proceed with the neighbor. If the neighbor is not greater, then the current measurement value is selected as the peak value. Rather than use only adjacent neighbors to the current measurement value, a sliding window of neighbors may be considered. Different methods may be applied to identifying a peak value without departing from the scope of the invention. Further, the processing of a contiguous region to identify a peak value may identify multiple peak values. If multiple peak values are identified, then each peak value may be analyzed together or individually below.

In Step 509, a number of contiguous values that are greater than a threshold value and include the peak value are determined. In other words, contiguous measurement values that are each greater than the threshold value are determined to be part of the same peak. If two peak values exist that have contiguous values greater than the peak size threshold and connecting the two peak values, the two peak values may be determined to be part of the same peak or separated into two peaks. The decision to separate may be performed based on the distance between the two peak values, the relative magnitude of the two peak values to each other, or other factors. The separation may be performed by identifying a local minimum between the two peak values and separating at the local minimum in one or more embodiments. In one or more embodiments, the separation may be performed by identifying a midpoint between the two peak values and separating at the midpoint in one or more embodiments. Other techniques may be used to perform the separation without departing from the scope of the invention.

In Step 511, a peak size of the peak is determined based on the number of contiguous values in accordance with one or more embodiments of the invention. In one or more embodiments of the invention, the peak size may be determined by counting the number of pixels in the peak. For example, the number of pixels included in the count may be the total number of pixels in the peak (e.g., area), along the maximum width or length of the peak, and/or along a different dimension. Rather than or in addition to using numbers of pixels, other units of measurements may be used.

In Step 513, a variability indicator in the number of peaks of the contiguous region over time is determined. As discussed above, the variability indicator identifies how the number of peaks changes over the period of several frames. Determining the variability indicator may be performed by identifying the difference between the number of peaks in the each frame as compared to the immediately preceding frame. The number of consecutive non-zero differences within the period of the frames may be identified as the variability indicator. By way of another example, the variability indicator may further account for the magnitude of the difference, such as by adding the differences.

In Step 515, a determination is made whether moisture is detected in accordance with one or more embodiments of the invention. The various indicators may be combined to determine whether moisture is present. In some embodiments, the concavity parameter is a primary indicator of the presence of moisture. In such embodiments, the peak size and the variability indicator are secondary indicators of moisture. For example, the peak size and/or the variability indicator may be used to validate that moisture is present when concavity indicates the presence of moisture. In other embodiments, peak size and/or variability indicator are primary indicator(s) and the concavity parameter is secondary. In other embodiments, each indicator is given equal weight. Determining whether moisture is present may be performed by comparing each indicator with a respective threshold that is defined for the indicator. The following discussion describes how each indicator may be used to detect the presence of moisture.

In the presence of moisture, an input object may move through one or more droplets on the sensing region. As the input object moves through the droplets, the droplets may be combined to form a larger region that is connected to the input object. Through the connection of the liquid to the input object, the connected and now combined droplets are detectable in the capacitive image as a single contiguous region. Because of the movement, the contiguous region has an irregular shape that may be concave. Thus, the concavity parameter may indicate the presence of moisture. However, a concave contiguous region may be due to a pinching gesture. Thus, if secondary indicators do not indicate a presence of moisture even when the concavity indicator indicates the presence of moisture, moisture may not be detected in Step 515. In such a scenario, two input objects may be detected for the contiguous region. For example, a pinch gesture may be detected.

Continuing with the indicators, in the presence of moisture, an input object in a puddle may have a larger peak than an input object not in a puddle. In other words, the peak of the input object in a liquid would be a lower and more spread out than the peak of an input object without moisture. Without moisture, the peak is generally sharper (i.e., has a greater slope to the peak) and taller than with moisture.

Further, in the presence of moisture, the number of peaks may change erratically as an input object moves through droplets or larger puddles. The change may be faster than any user is likely to change or possibly even capable of changing. Thus, greater variability in the number of peaks over time may indicate the presence of moisture.

If moisture is not detected, the flow may proceed to Step 519 to determine whether another unprocessed contiguous region exists. If another unprocessed contiguous region exists, the flow may return to Step 503 to process the next contiguous region. If moisture is not detected, the shape of the contiguous region may be used to estimate orientation of the input object, improve positional accuracy, improve snap distance, and/or perform other action. Further, positional information may be determined and reported to the host device. A user interface action may be performed based on the positional information. For example the user interface action may be changing the host device from a low power mode, opening an application, updating the display, performing another action, or any combination thereof.

If moisture is presence, the system operates based on the presence of moisture in Step 517. As discussed above, the presence of moisture affects the capacitive image, and, thus, may affect the resulting positional information for input object(s) in the sensing region. The operation based on the presence of moisture may include reporting the presence of moisture and/or mitigating the effects of moisture on the contiguous region. Further, operating based on the presence of moisture may be for the particular contiguous region in which moisture is detected or for the entire capacitive image. For example, each contiguous region may be treated individually with regards to whether to operate based on the presence of moisture. By the way of another example, once moisture is detected for any contiguous region, the system may enter a moisture management state for each contiguous region and operate accordingly.

Figure 6:
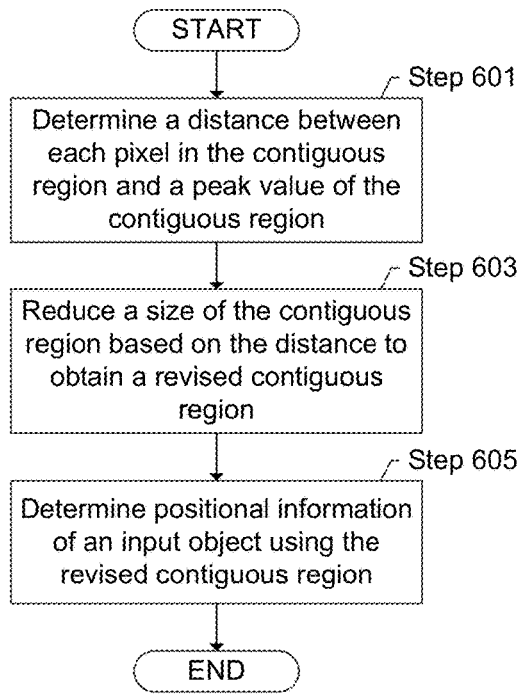
Figure 7:
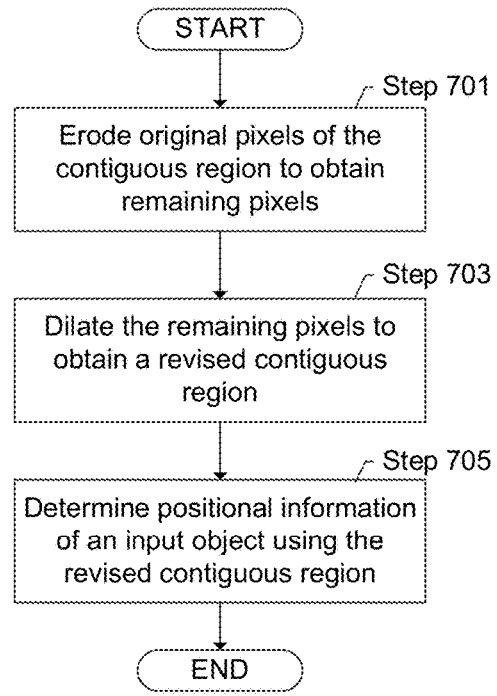

FIGS. 6 and 7 show flowcharts for mitigating the effects of moisture in accordance with one or more embodiments of the invention. FIG. 6 shows a flowchart for determining positional information based on distance to a peak. In Step 601, a distance between each pixel in the contiguous region and a nearest peak value of the contiguous region in accordance with one or more embodiments of the invention. Determining the distance may be based on a straight line distance or a number of pixels between the pixel and the nearest peak value.

In Step 603, the size of the contiguous region is reduced based on the distance to obtain a revised contiguous region in accordance with one or more embodiments of the invention. In other words, for each pixel, a determination is made whether the distance of the pixel to the nearest peak value is greater than a distance threshold. If the distance is greater than the distance threshold the pixel is removed from the contiguous region. In some embodiments, rather than determining and using the distance to the nearest peak value, the distance to the greatest peak value may be determined and used. Once all pixels are processed, the result of the removal is a revised contiguous region that is smaller than the contiguous region in Step 601.

In Step 605, positional information of an input object is determined using the revised contiguous region. For example, the position of the input object may be determined to be in the center of the revised contiguous region. Other techniques for determining the positional information may be used. As discussed above, the positional information may be reported to the host device and/or used to perform a user interface action.

FIG. 7 shows a flowchart for determining positional information based on eroding the contiguous region. In Step 701, original pixels in the contiguous region are eroded to obtain remaining pixels. The erosion may be performed as follows. The processing may proceed by iteratively considering each original pixel. When an original pixel is considered, the pixel may be referred to as a current pixel. For each current pixel, a determination may be made whether any neighbor original pixel that is adjacent (or within a pre-defined distance) to the original pixel is not in the contiguous region. If a neighbor is not in the contiguous region, the current pixel is removed. If all neighbors are in the contiguous region, the current pixel remains and becomes a remaining pixel.

In Step 703, the remaining pixels are dilated to obtain a revised contiguous region. Dilating is a reverse process of the eroding. In other words, the dilation may be performed as follows. The processing may proceed by iteratively considering each remaining pixel. When a remaining pixel is considered, the pixel may be referred to as a current pixel. The current pixel is set in the revised contiguous region. Further, for each current pixel, a determination may be made whether any neighbor remaining pixel that is adjacent (or within a pre-defined distance) to the original pixel is not in the contiguous region. If a neighbor is not in the contiguous region, the neighbor is added to the revised contiguous region. Once all pixels are processed, the result of the dilation is a contiguous region that is more convex and may be smaller than in Step 701.

In Step 705, positional information of an input object is determined using the revised contiguous region. For example, the position of the input object may be determined to be in the center of the revised contiguous region. Other techniques for determining the positional information may be used. As discussed above, the positional information may be reported to the host device and/or used to perform a user interface action.

Although the above description presents several distinct flowcharts, the various flowcharts may be combined in various embodiments of the invention. In other words, one or more embodiments are not limited to the steps of a single flowchart or even the ordering of steps in a single flowchart. For example, the steps 601, 603, 701, 703, and 605/705 of FIGS. 6 and 7 may be performed to mitigate the effects of moisture.

Figure 8:
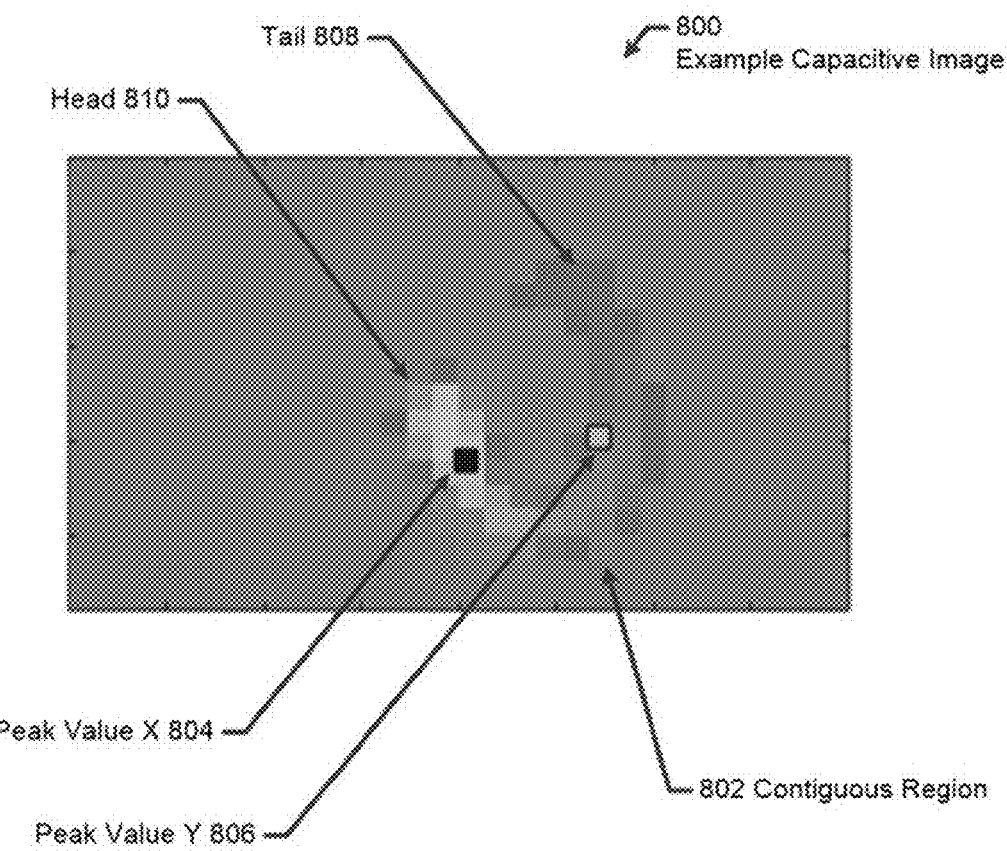
Figure 9:
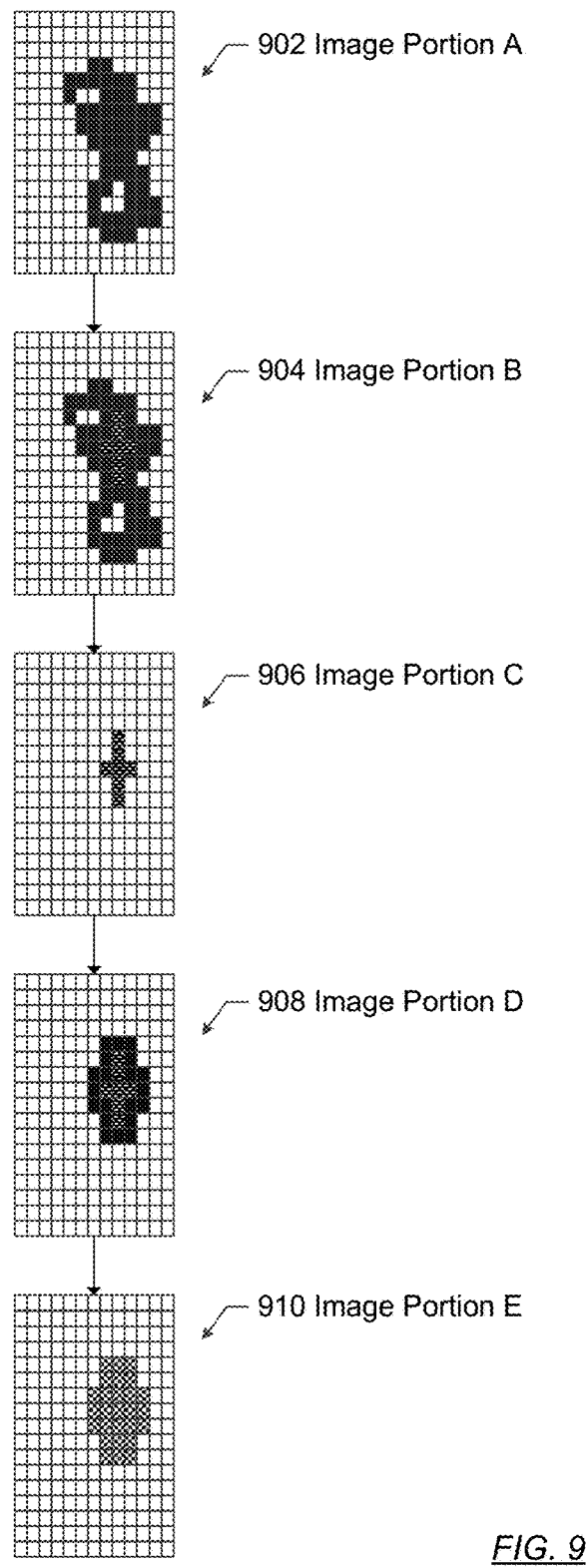

The following examples are for explanatory purposes only and not intended to limit the scope of the invention. FIGS. 8, 9, 10.1, 10.2, and 10.3 are examples in accordance with one or more embodiments of the invention.

FIG. 8 shows an example of a capacitive image (800) with a contiguous region (802) having two peak values (e.g., peak value X (804), peak value Y (806)). Contiguous region (802) may be caused, for example, by a user dragging a finger starting at the tail (808) through several droplets to the head (810) as shown by the path of the contiguous region. When the user drags the user's finger through the droplets, the droplets may connect to form the shape. However, to the capacitive input device, moisture is detected based on the capacitive image and not prior knowledge of droplets. Thus, based at least in part on the shape of the contiguous region (802) being convex, the determination may be made that moisture is present. Further, based on the relative magnitudes of the peaks, peak value X (804) may be determined to correspond to a user's finger, while peak value Y (806) may be determined to correspond to a ghost finger (i.e., a finger that does not exist). By determining that moisture is present, mitigation of the moisture may be performed to obtain a more accurate estimate of position of the input object.

FIG. 9 shows a consecutive set of the same portion of a capacitive image for mitigating the effects of moisture. Image Portion A (902) shows an original contiguous region (shown with black fill) prior to mitigating the effects of moisture. As shown, the original contiguous region is concave. Image Portion B (904) shows pixels that will be removed by erosion of the contiguous region. In particular, the adjacent neighbors of each pixel is determined and only pixels having all adjacent neighbors present remains in the portion of the capacitive image. The black fill in Image Portion B (904) indicates the pixels to be removed while the patterned fill indicates the pixels that remain. Image Portion C (906) shows the result after the erosion is performed. As shown, only the patterned filled pixels remain, which each have all adjacent neighbors.

Image Portion D (908) shows pixels that will be added by dilation of the contiguous region. In particular, the adjacent neighbors of each pixel are added to the contiguous region. The black fill in Image Portion D (908) indicates the pixels to be added while the patterned fill indicates the pixels that are in Image Portion C (906). Image Portion E (910) shows the result after the dilation is performed. As shown, the result is a concave region, which may be a more accurate estimate of the input object. The input object may be detected as being located in the middle of the contiguous region in Image Portion E (910). Thus, the effects of the droplets may be mitigated.

FIGS. 10.1, 10.2, and 10.3 show a set of diagram for mitigating the effects of moisture in the contiguous region based on distance. In particular, FIG. 10.1 shows a portion of a capacitive image (1000) with a contiguous region. As shown, the contiguous region (1002) is convex. Position A (1004) and position B (1006) are possible locations of the input object without accounting for the effects of moisture. As shown, neither estimate may be accurate.

FIG. 10.2 shows a pixelated version of the portion of the capacitive image showing a process of mitigation. In particular, Image A (1008) shows the contiguous region. Image B (1010) shows pixels that will be removed based on distance to the peak of the contiguous region. In particular, the farther pixels are removed. The darker fill in Image B (1010) indicates the pixels to be removed while the lighter fill indicates the pixels that remain. Image C (1012) shows the pixels the revised contiguous region (1014) with the pixels removed.

The input object may be detected as being located in the middle of the revised contiguous region in Image C (1010). FIG. 10.3 shows the portion of the capacitive image (1000) with the detected position (1016) of the input object after the effects of moisture are mitigated. Thus, the effects of the droplets may be mitigated.

Thus, the embodiments and examples set forth herein were presented in order to best explain the present invention and its particular application and to thereby enable those skilled in the art to make and use the invention. However, those skilled in the art will recognize that the foregoing description and examples have been presented for the purposes of illustration and example only. The description as set forth is not intended to be exhaustive or to limit the invention to the precise form disclosed.

What is claimed is:

1. A processing system for moisture detection comprising:
   sensor circuitry for obtaining absolute capacitive sensor data; and
   processing circuitry configured to:
   determine a contiguous region in a capacitive image generated based on the absolute capacitive sensor data,
   determine a concavity parameter of the contiguous region, wherein the concavity parameter is based on a two-dimensional geometry of the contiguous region in the capacitive image, determined in a plane parallel to an input surface of a sensing region from which the absolute capacitive sensor data were obtained, with a concavity described by the concavity parameter being assessed in the plane, in the capacitive image, detect a presence of moisture based at least in part on the concavity parameter, and operate based on the presence of moisture.

2. The processing system of claim 1, wherein the processing circuitry is further configured to:

determine a peak value of the contiguous region;

determine a number of contiguous values that are greater than a threshold value and comprise the peak value; and determine a peak size of the peak based on the number of contiguous values, wherein detecting the presence of moisture is further based on the peak size.

3. The processing system of claim 1, wherein the processing circuitry is further configured to:

determine a variability indicator in a number of peaks of the contiguous region over time, wherein detecting the presence of moisture is further based on the variability indicator.

4. The processing system of claim 1, wherein operating based on the presence of moisture comprises:

mitigating effects of moisture in the contiguous region.

5. The processing system of claim 4, wherein mitigating effects of moisture comprises:

determining a distance between each pixel in the contiguous region to a peak value of the contiguous region;

reducing a size of the contiguous region based on the distance to obtain a revised contiguous region;

determining positional information of an input object using the revised contiguous region.

6. The processing system of claim 4, wherein mitigating effects of moisture comprises:

eroding a plurality of original pixels of the contiguous region to obtain a plurality of remaining pixels;

dilating the plurality of remaining pixels to obtain a revised contiguous region; and determining positional information of an input object using the revised contiguous region.

7. The processing system of claim 1, wherein the sensor circuitry is configured to connect to a plurality of sensor electrodes disposed in a matrix array, wherein each sensor electrode of the plurality of sensor electrodes represents a pixel in the capacitive image, and wherein the sensor circuitry is configured to obtain the absolute capacitive sensor data using the plurality of sensor electrodes.

8. A method for moisture detection comprising:

obtaining absolute capacitive sensor data;

determining a contiguous region in a capacitive image generated based on the absolute capacitive sensor data;

determining a concavity parameter of the contiguous region, wherein the concavity parameter is based on a two-dimensional geometry of the contiguous region in the capacitive image, determined in a plane parallel to an input surface of a sensing region from which the absolute capacitive sensor data were obtained, with a concavity described by the concavity parameter being assessed in the plane, in the capacitive image;

detecting a presence of moisture based at least in part on the concavity parameter; and operating based on the presence of moisture.

9. The method of claim 8, further comprising:

determining a peak value of the contiguous region;

determining a number of contiguous values that are greater than a threshold value and comprise the peak value; and determining a peak size of the peak based on the number of contiguous values, wherein detecting the presence of moisture is further based on the peak size.

10. The method of claim 8, further comprising:

determining a variability indicator in a number of peaks of the contiguous region over time, wherein detecting the presence of moisture is further based on the variability indicator.

11. The method of claim 8, wherein operating based on the presence of moisture comprises:

mitigating effects of moisture in the contiguous region.

12. The method of claim 11, wherein mitigating effects of moisture comprises:

determining a distance between each pixel in the contiguous region to a peak value of the contiguous region;

reducing a size of the contiguous region based on the distance to obtain a revised contiguous region;

determining positional information of an input object using the revised contiguous region.

13. The method of claim 11, wherein mitigating effects of moisture comprises:

eroding a plurality of original pixels of the contiguous region to obtain a plurality of remaining pixels;

dilating the plurality of remaining pixels to obtain a revised contiguous region; and determining positional information of an input object using the revised contiguous region.

14. The method of claim 8, wherein operating based on the presence of moisture comprises:

reporting the presence of moisture in the contiguous region.

15. The method of claim 8, wherein the absolute capacitive sensor data are obtained from sensor circuitry, configured to be connected to a plurality of sensor electrodes disposed in a matrix array, and wherein each sensor electrode of the plurality of sensor electrodes represents a pixel in the capacitive image, and wherein the sensor circuitry is configured to obtain the absolute capacitive sensor data using the plurality of sensor electrodes.

16. An input device for moisture detection comprising:

sensor electrodes for obtaining absolute capacitive sensor data; and a processing system configured to:

determine a contiguous region in a capacitive image generated based on the absolute capacitive sensor data, determine a concavity parameter of the contiguous region, wherein the concavity parameter is based on a two-dimensional geometry of the contiguous region in the capacitive image, determined in a plane parallel to an input surface of the input device, with a concavity described by the concavity parameter being assessed in the plane, in the capacitive image, detect a presence of moisture based at least in part on the concavity parameter, and operate based on the presence of moisture.

17. The input device of claim 16, wherein the processing system is further configured to:

determine a peak value of the contiguous region;

determine a number of contiguous values that are greater than a threshold value and comprise the peak value; and determine a peak size of the peak based on the number of contiguous values, wherein detecting the presence of moisture is further based on the peak size.

18. The input device of claim 16, wherein the processing system is further configured to:
  determine a variability indicator in a number of peaks of the contiguous region over time,
  wherein detecting the presence of moisture is further based on the variability indicator.

19. A processing system for moisture detection comprising:
  sensor circuitry for obtaining absolute capacitive sensor data; and
  processing circuitry configured to:
    determine a contiguous region in a capacitive image generated by the absolute capacitive sensor data;
    determine a concavity parameter of the contiguous region;
    detect, based on a secondary indicator, an absence of moisture even when the concavity parameter indicates a presence of moisture; and
    determine a presence of at least two input objects based on the contiguous region, the concavity parameter, and the absence of moisture.

20. A method for moisture detection comprising:
  obtaining absolute capacitive sensor data;
  determining a contiguous region in a capacitive image generated by the absolute capacitive sensor data;
  determining a concavity parameter of the contiguous region;
  detecting, based on a secondary indicator, an absence of moisture even when the concavity parameter indicates a presence of moisture; and
  determining a presence of at least two input objects based on the contiguous region, the concavity parameter, and the absence of moisture.

* * * * *